United States Patent [19]

Székely et al.

[11] 4,281,170
[45] Jul. 28, 1981

[54] PROCESS FOR THE PREPARATION OF PYRETHRINS AND ANALOGUES THEREOF AND INSECTICIDAL COMPOSITIONS CONTAINING THE SAME

[75] Inventors: István Székely, Szentendre; Marianna Lovász née Gáspár, Budapest, Gábor Kovacs, Rudolf Soós, Budapest; Lajos Nagy, Szentendre; Bela Kószegi, Budapest, all of Hungary

[73] Assignee: Chinoin Gyógyszer és Vegyészeti Termékek Gyára Rt, Budapest, Hungary

[21] Appl. No.: 13,070

[22] Filed: Feb. 21, 1979

[30] Foreign Application Priority Data

Feb. 23, 1978 [HU] Hungary .................... CI 1814

[51] Int. Cl.³ ............... C07C 69/747; C07C 67/297; C07C 69/743
[52] U.S. Cl. ...................................... 560/124
[58] Field of Search ............................. 560/124

[56] References Cited

U.S. PATENT DOCUMENTS

| | | | |
|---|---|---|---|
| 2,603,652 | 7/1952 | Schechter | 560/124 |
| 2,661,374 | 12/1954 | Schechter | 560/124 |
| 2,768,965 | 10/1956 | Stansburg | 560/124 |
| 2,891,888 | 6/1959 | Guest | 560/124 |
| 2,891,889 | 6/1959 | Haynes | 560/124 |
| 3,009,946 | 11/1961 | Takei | 560/124 |
| 3,282,985 | 11/1966 | Matsui | 560/124 |
| 3,284,486 | 11/1966 | Matsui | 560/124 |
| 3,636,059 | 1/1972 | Matsui | 560/124 |
| 3,998,868 | 12/1976 | Mizutani | 560/124 |
| 4,024,163 | 5/1977 | Elliott | 560/124 |

OTHER PUBLICATIONS

Szekely, Tetrahedron letters, 49 pp. 4505–4506 (1976).
Tomoskozi, Tetrahedron Letters, 50, pp. 4639–4642 (1976).
Hilgetafg "Preparative Organic Chemistry," pp. 368–381 (1972).
"The Peptides," vol. 1 p. 212 (1965) Academic Press.

Primary Examiner—Natalie Trousof
Assistant Examiner—Michael L. Shippen
Attorney, Agent, or Firm—Karl F. Ross

[57] ABSTRACT

A method of making an insecticidal pyrethrin by oxidation in aprotic organic solvent. The compounds are of the formula:

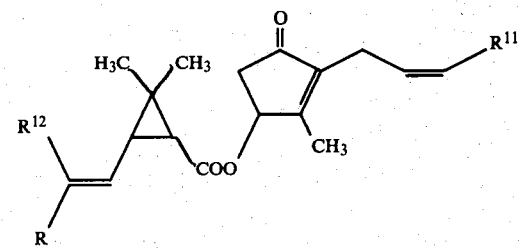

wherein
$R^{11}$ is straight or branched chain lower alkyl or 1-alkenyl or hydrogen;
R and $R^{12}$ are the same or different and are hydrogen, halogen or lower alkyl or one of the moieties R and $R^{12}$ is lower alkoxycarbonyl.

10 Claims, No Drawings

PROCESS FOR THE PREPARATION OF PYRETHRINS AND ANALOGUES THEREOF AND INSECTICIDAL COMPOSITIONS CONTAINING THE SAME

CROSS REFERENCE TO RELATED APPLICATION

This application is related to Applicants' copending application Ser. No. 013,069 filed Feb. 21, 1979.

This invention relates to a new process for the preparation of pyrethrins and analogs thereof.

More particularly our invention is concerned with the preparation of optically active or racemic pyrethrin derivatives of the formula I

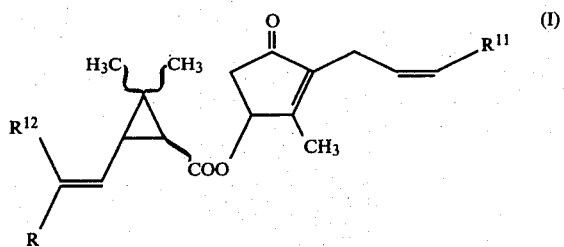

wherein
$R^{11}$ is straight or branched chain lower alkyl or 1-alkenyl or hydrogen;
R and $R^{12}$ are the same or different and are hydrogen, halogen or lower alkyl or one of the moieties R and $R^{12}$ may also stand for lower alkoxycarbonyl;
the ∼ valency bonds represent α- and/or β-configuration; the—valency bond represents β-configuration.

In the new process of the present invention the optically active or racemic compounds of the formula I are prepared by subjecting an optically active or racemic chrysanthemic acid ester derivative of the formula II

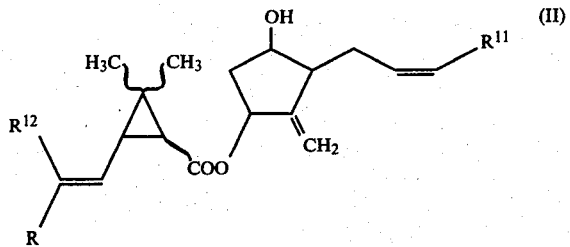

(wherein $R^{11}$, R and $R^{12}$, ∼ and—have the same meanings as stated above) to oxidation by treatment with an oxidizing agent in an aprotic inert organic solvent. The oxidizing agent oxidizes the free hydroxy group in position 1β of the starting material of the formula II into an oxo group and the said oxidation is followed by spontaneous re-arrangement of the exocyclic double bond (3-methylene group) into an endocyclic double bond.

The term "lower alkyl" relates to straight or branched chain alkyl having 1-4 carbon atoms (e.g. methyl, ethyl, n-propyl, isopropyl and n-butyl). The term "1-alkenyl-" covers straight or branched chain lower alkenyl having 2-5 carbon atoms (e.g. vinyl and prop-1-enyl). The term "lower alkoxycarbonyl" relates to alkoxycarbonyl groups having an alkoxy moiety of 1-4 carbon atoms (e.g. methoxycarbonyl and ethoxycarbonyl etc.). The term "halogen" encompasses the fluorine, chlorine, bromine and iodine atoms.

According to a preferred embodiment of the present invention there is provided a new process for the preparation of compounds of the formula I, wherein $R^{11}$ is hydrogen or lower alkyl; R and $R^{12}$ are lower alkyl, R and $R^{12}$ are particularly methyl and $R^{11}$ is particularly hydrogen, methyl or ethyl.

The compounds of the formula I are valuable insecticides and may be used as the active ingredients of insecticidal compositions.

Insecticidal compositions containing as active ingredient pyrethrin derivatives have already been disclosed before but the insecticidal compositions comprising as active ingredient a compound of the formula I prepared according to the process of the present invention are superior to the known insecticidal compositions. The known compositions were prepared by using the so-called "pyrethrum extract", which is isolated from vegetable drugs and thus contains mainly unidentified further components in addition to the desired insecticidal pyrethrins and are possibly detrimental to the health. Thus these known compositions may cause undesired toxical side effects. The compositions prepared according to the present invention however contain a homogeneous well-defined active ingredient and are free of toxic impurities. The present invention provides a further advantage in making it possible to overcome resistance by substituting another compound of the formula I as the active ingredient in an insectidical composition.

According to the present invention there are also provided insecticidal compositions containing as active ingredient a compound of the formula I (wherein R, $R^{12}$ and $R^{11}$ have the same meanings as stated above) prepared according to the above process, optionally in admixture with usual additives, carriers, excipients and-/or further biologically active compounds.

The additives, carriers and excipients may be those generally used in the formulation of insecticidal compositions and can be solid, liquid, or gaseous substances. The solid carriers can be various organic or inorganic meals (such as artificial or natural ground stones, e.g. kaolin, China clay, powdered silica, bentonite, fuller's earth, wood flour etc.). As liquid carriers organic solvents can be mentioned (e.g. saturated or unsaturated hydrocarbons, alkanols, such as ethanol; ketones e.g. acetone; esters such as ethyl acetate; and dimethyl sulfoxide, dimethylformamide etc.). Optional mixtures of the said organic solvents can be used as well. As gaseous carriers, preferably carbon dioxide and the mixtures of halogenated hydrocarbons are used.

The insecticidal compositions of the present invention can also contain further biologically active components which may synergize or accelerate the action of the active ingredient of the formula I. For this purpose piperonyl butoxide can be used.

The insecticidal compositions of the present invention can be formulated in solid or liquid form. Thus they can be in the form of dusting-powder mixtures, spray, aerosols, etc.

According to a preferred embodiment of the present invention the compounds of the formula I prepared by the process claimed are formulated as aerosols. Such compositions are used to kill the noxious insects preying on humans and domestic animals and the low mammal toxicity of the said compositions is very advantageous.

The insecticidal compositions of the present invention may be prepared by methods known per se. The methods comprise the proper admixture of the active ingredient with various suitable, solid, liquid or gaseous carriers, excipients and other additives. The formulations may be prepared by conventional techniques such as by stirring, admixing, grinding or dissolving.

The optically active and racemic compounds of the formula I comprise natural pyrethrins and analogs thereof. Natural pyrethrins possess outstanding insecticidal properties. They exhibit insecticidal activity at very low concentrations and are practically atoxic against mammals. The additional effects (knock-down and repellent effect) are excellent as well. Although natural pyrethrins have been used for more than hundred years, significant resistance has not developed. Contrary to insecticides of other type, the use of natural pyrethrins as insecticides in the environment of humans and in agriculture is of great advantage and more and more popular from the point of view of the protection of the environment.

Natural pyrethrins occur in the oil extracted from the flower of the plant Chrysanthemum cinerariefolium in admixture with other non-insecticidal compounds, such as fatty acids, sterols, flavanoids, chlorophyl. The said plant grows in tropical countries.

The structure of the six components of the so-called "pyrethrum extract" is shown in Table I. The compounds correspond to the formula IV

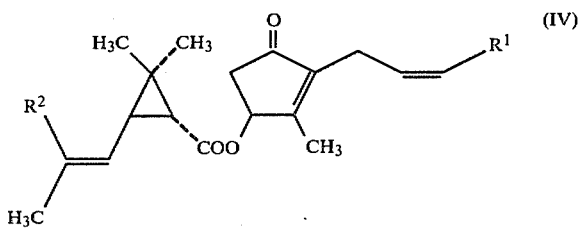

(IV)

TABLE I

| Name | R¹ | R² |
| --- | --- | --- |
| Pyrethrin I | vinyl | methyl |
| Pyrethrin II | vinyl | methoxycarbonyl |
| Cinerin I | methyl | methyl |
| Cinerin II | methyl | methoxycarbonyl |
| Jasmolin I | ethyl | methyl |
| Jasmolin II | ethyl | methoxycarbonyl |

It may be seen that the compounds of the series "I" are esters of chrysanthemic acid (R² is methyl) and those of the series "II" are esters of pyrethrinic acid (R² is methoxycarbonyl) formed with rethrolones i.e. cyclopentenone-alcohols. Both the acid and alcohol components of said esters contain one or more chiral centers and thus both components may be present in racemic or optically active forms.

It is difficult to prepare these compounds from plants in pure form. Due to the very close physico-chemical relationship of the molecules, the separation thereof can be carried out only by means of extraordinarily lengthy, circumstantial and expensive chromatographic methods whereby generally partial epimerization takes place.

Nevertheless in some cases the individual components can be separated. It is also known that the activity and stability of the components of "pyrethrum extract" may differ to a great extent.

Thus pyrethrin I and cinerin I have a stronger activity than jasmolin I [J. Science of Food and Agriculture, Vol. 13., 260 (1962)]. On the other hand cinerin I and jasmolin I are significantly more stable than pyrethrin I [Pyrethrum Post, Vol. 9, 17 (1968)]. There has been a long need for the synthetic preparation of pyrethrins and related compounds (pyrethroids). The closest compounds to natural pyrethrins ever prepared by a synthetic route are bioallethrin and S-bioallethrin (compounds of the formula IV, wherein R¹ is methyl and R² is hydrogen). The first compound is the ester of d-(+)-trans-chrysanthemic acid with racemic allethronole, while the latter is the ester of d-(+)-trans-chrysanthemic acid formed with dextrorotatory (+)-allethrolone. It is known also that the insecticidal activity of S-bioallethrin is several times higher than that of bioallethrin (Dutch Patent Application No. No. 7.413.401).

There are known some methods for the total synthesis of racemic "natural" pyrethrins. A summary review can be found in the book "Pyrethrum, The Natural Insecticide" [Editor: J. E. Casida; Academic Press, N.Y., London (1963)].

As to the synthesis of optically active pyrethrins having the same configuration as the natural pyrethrins only the theoretical possibility existed of the resolution of racemic rethrolone and acylation of the corresponding optically active isomer with d-(+)-transchrysanthemic acid.

The resolution of racemic rethrolones is a rather complicated and uneconomical process. It is known that resolution may be carried out via the corresponding semicarbazide [J. Org. Chem., 29, 5225 (1964)].

In the preparation of optically active compounds in order to improve the economic efficiency of the process it is advantageous to carry out resolution at an early stage of the synthesis.

The process of the present invention is the first industrial scale method suitable for the preparation of optically active pyrethrins having the same configuration as natural pyrethrins and also for the production of several related pyrethrin analogs hitherto never described in prior art. The above process can also be used for the preparation of S-bioallethrin.

According to the known methods pyrethrins were prepared by acylation of racemic rethrolones with chrysanthemic acid derivatives. In the course of the preparation of the racemic rethrolones, the hydroxy group to be acylated was first protected and after the formation of the rethrolone molecule the said protecting group was removed prior to acylation. It is known however [Chem. and Ind., 1142 (1966)] that rethrolone(s) are unstable compounds and therefore the introduction and elimination of the protecting group may cause considerable decomposition and this may decrease the yield and the optical purity of the product (when optically active compounds are prepared). The removal of the products of decomposition may necessitate additional complicated separation steps.

It has been surprisingly found that the above difficulties may be overcome by the following preparation of pyrethrins and analogs thereof:

The hydroxymethyl group of 3,3aα,4,5,6aα-hexahydro-2-oxo-4α-hydroxymethyl-5β-hydroxy-2H-cyclopenta[b]furan [see Tetrahedron Letters, 50, 4639–42 (1976)] is subjected to selective halogenation, the 4α-halogenomethyl-lactone derivative thus obtained is reduced in a manner known per se, the lactol thus obtained is alkylated by means of a Witting reaction to form the characteristic cis-alkenyl side-chain of the rethrolone structure and the halogenomethyl side-chain is subjected to dehydrohalonation. The 2-substituted- 1,4-dihydroxy-3-methylene-cyclopentane derivative thus obtained is selectively acylated on the hydroxy group in the 4 position and thus the new starting materials—pyrethrin-precursors—of the formula II are obtained. As aclyating agent the corresponding chrysanthemic acid derivative is used. Since in the course of the selective acylation it is exclusively the hydroxy-group in the 4 position which is acylated, the necessity of introduction and removal of a protecting group is eliminated and there is provided a new and suitable method for the preparation of pyrethrins containing optically active rethrolone components by good yields.

The oxidation process of the present invention is carried out in an aprotic inert organic solvent. As the reaction medium aromatic, aliphatic or alicyclic hydrocarbons (e.g. benzene, toluene, cyclohexane, petrolether etc.), halogenated hydrocarbons (e.g. dichloromethane or dichloroethane etc.), ketones (e.g. acetone, or methylethyl-ketone) can be used. One can also use solvents such as dimethyl sulfoxide or optional mixtures of these solvents.

The scope of oxidizing agents which may be applied in the process of the present invention is very broad. Practically any oxidizing agent can be used which is capable of oxidizing the secondary hydroxy group attached to the cyclopentane ring into an oxo group without substantially damaging the other parts of the molecule. The following oxidizing agents are enumerated only as examples without the intention of any limitation.

(a) Oxidizing agents containing a chromium$^{6+}$ atom, such as Jones-reactant [*J. Chem. Soc.*, 39 (1946)]; Fieser reactant [*J. Am. Chem. Soc.*, 70, 3237 (1948)]; Sarrett reactant [*J. Am. Chem. Soc.*, 75, 422 (1953)]; Conforth reactant [*Tetrahedron Letters*, 18, 1351 (1962)]; Collins and modified Collins reactant [*Tetrahedron Letters*, 3363 (1968) and *J. Org. Chem.* 35, 4000 (1970)]; pyridinium-chlorochromate reactant [*Tetrahedron Letters*, 2647 (1975)]; sodiumdichromate-sulfuric acid-dimethyl-sulfoxide reactant [*J. Org. Chem.*, 39, 3304 (1974)]; pyridinium-dichromate reactant [*Chem. Comm.*, 752 (1966)]; and the pyrazole-chromo trioxide reactant [*Carbohydrate Res.*, 12 147 (1970)].

(b) Oxidizing agents which exert their oxidizing effect by the formation of a sulfoxonium-salt type intermediate product, such as dimethyl sulfoxide—phosphorous pentoxide reactant [*J. Am. Chem. Soc.*, 87, 4651 (1965)]; dimethyl sulfoxide-acetic anhydride reactant [*J. Am. Chem. Soc.*, 87, 4214 (1965) and *J. Am. Chem. Soc.*, 89, 2416 (1967)]; dimethyl sulfoxide-tosyl- or benzoyl chloride and dimethyl-sulfoxide-tosyl- or mesyl anhydride reactant [*J. Org. Chem.*, 39, 1977 (1974)]; dimethylsulfoxide-chlorine reactant [*Tetrahedron Letters*, 919 (1973)]; dimethyl sulfoxide-sulfur trioxide reactant [*J. Am. Chem. Soc.*, 89, 5505 (1967)]; dimethyl sulfoxide-chlorine-triethylamine reactant [*J. Am. Chem. Soc.*, 94, 7586 (1972)]; thioanisol-chlorine-triethylamine reactant [*J. Org. Chem.*, 38, 1233 (1973)] and the Pfitzner-Moffatt oxidation [*J. Am. Chem. Soc.*, 85, 3207 (1963)].

(c) Other oxidizing agents generally used in organic chemistry such as ruthenium tetroxide [*Rev. Pure Appl. Chem.*, Australia, 22, 47 (1968)], Fetizon reactant [silver carbonate on *Celite, Compt. Rend. Set. C.*, 267, 900 (1968)]; iodobenzene-dichloride reactant [*Tetrahedron Letters*, 3635 (1973)] or chlorine-pyridine reactant [*Tetrahedron Letters*, 3059 (1974)].

The reaction temperature depends on the oxidizing agent used and generally ranges between −70° C. and +80° C. At elevated temperatures side reactions may take place, while at lower temperatures the reaction velocity decreases.

The reaction can be followed by thin-layer chromatography. The reaction having been finished, the compounds of the formula I can be isolated by extraction or filtration and subsequent evaporation of the reaction mixture. The product obtained can be purified by means of column chromatography if desired.

Further details of the present invention are to be found in the Examples which serve merely for illustration and not limitation.

EXAMPLE 1

2 g. (6.28 millimoles) of 1β-hydroxy-2β-(but-2-cisenyl)-3-methylene-cyclopentan-4β-yl-(+)-trans-chrysanthemate are dissolved in 18 ml. of acetone (distilled over potassium permanganate). The solution is cooled to a temperature between 0° C. and −5° C. whereupon at this temperature a solution of 3.52 ml. (9.4 2 millimoles) of Jones-reactant in 23 ml. of concentrated sulfuric acid (diluted with water to 100 ml.) is added under stirring within an hour. The reaction is monitored by thin-layer chromatography (silica gel, developing agent 4:1 mixture of petroleum ether and ethyl acetate). Thirty minutes after the termination of the addition the excess of the oxidizing agent is decomposed by adding 2 ml of isopropanol and the reaction mixture is diluted with up to 50 ml. of water. The aqueous phase is extracted three times with 30 ml. of petroleum ether each, the organic layers are combined, dried over anhydrous sodium sulfate and evaporated in vacuo at a temperature below 40° C. Thus 1.9 g. of the crude product are obtained.

The crude product thus obtained is subjected to chromatography on 100 g. of silica gel by using a 4:1 mixture of petroleum ether and ethylacetate as eluting agent. The fractions corresponding to an $R_f$ value of 0.66 are collected and evaporated at a temperature below 40° C. in vacuo. Thus 1.51 g. of pure 3-methyl-2-(but-2-cisenyl)-1-oxo-cyclopent-2-en-4β-yl-(+)-trans-chrysanthemate (Cinerin I) are obtained. Yield: 76.3%.

$R_f$=0.66 (on a "Merck" silica-gel plate, developing agent: 4:1 mixture of petroleum ether and ethylacetate).

IR(film): $v_{max.}$=at 2900, 1715, 1660, 1180, 1140, 1100 and 840 cm$^{-1}$.

EXAMPLE 2

0.3 g. of (1.4 millimoles) of a pyridinium-chlorine-chromate reactant [*Tetrahedron Letters*, 2647 (1975)] are suspended in 1 ml. of anhydrous methylene chloride, whereupon, at room temperature under stirring, 0.15 g. (0.47 millimoles) of 1β-hydroxy-2β-(but 2-cis-enyl)-3-methylene-cyclopentan-4β-yl-(+)-transchrysanthemate dissolved in 2 ml. of anhydrous methylene chloride are added to the suspensions. The suspension is stirred at room temperature for an hour, whereupon it is filtered through 6 g. of a filter aid ("Florisil" silica gel or "Celit"). The filter bed is washed with an additional 30 ml. of methylene chloride, the organic layers are combined and evaporated at a temperature below 40° C. in vacuo. Thus 0.129 g. of 3-methyl-2-(but-2-cis-enyl)-1-oxo-cyclopent-2-en-4β-yl-(+)-trans-chrysanthemate are obtained. Yield: 86%. The characteristic physical constants of this compound are identical with those of the product prepared according to Example 1.

EXAMPLE 3

To a solution of 273 mg. (2.13 millimoles) of N-chlorosuccinimide and 8.5 ml. of toluene at 0° C. 195 µg. (2.56 millimoles) of dimethyl sulfide are added under an inert gas (argon) atmosphere. The mixture is cooled to −25° C. under stirring in a carbon tetrachloride-dry ice cooling bath. At this temperature a solution of 0.156 g. (0.47 millimoles) of 1β-hydroxy-2β-(pent-2-cis-enyl)-3-methylene-cyclopentane-4β-yl-(+)-trans-chrysanthemate and 1 ml. of toluene is added dropwise. The reaction mixture is stirred at −25° C. for 2 hours, whereupon a solution of 435 mg. (4.3 millimoles) of triethylamine and 1 ml. of ether is added dropwise. The cooling bath is removed and 25 ml. of ether are added dropwise. The organic phase is washed with 10 ml. of 1% hydrochloric acid (temperature 0° C.) and twice with 10 ml. of water each and dried over anhydrous sodium sulfate. The solvent is distilled off in vacuo. Thus 140 mg. of 3-methyl-2-(pent-2-cis-enyl)-1-oxo-cyclopent-2-en-4β-yl-(+)-transchrysanthemate (Jasmolin I) are obtained. Yield: 93.3%. $R_f$=0.66 (on "Merck" 60 $F_{254}$ silica-gel plates; developing agent: 4:1 mixture of petroleum ether and ethylacetate).

IR (film): $\nu_{max.}$=2900, 1715, 1660, 1180, 1140, 1100 and 840 cm$^{-1}$.

NMR (CDCl$_3$): δ=5.7 (m, 1H, H-15), 5.2–5.6 (m, 2H-H-7 and H-8), 4.95 (m, 1H, H-4), 2.04 (s, 3H, H-11), 1.7 (m, 1H, H-14), 1.73 (s, 6H, H-20 and H-21), 1.14 and 1.27 (s and s), 3H and 3H, H-18 and H-19), 1.0 (t, 3H, H-10) ppm.

C$^{13}$ NMR (CDCl$_3$): δ=C-1 203.69; C-12 172.25; C-3 164.64; C-16 135.83; C-2 142.76; C-7 124.00; C-8 120.91; C-15 133.12; C-4 73.03; C-5 42.07; C-6 21.26; C-9 20.51; C-19 20.41; C-18 20.11; C-20 25.53; C-21 18.48; C-13 34.62; C-14 32.87; C-17 29.01; C-11 14.00; C-10 14.10 ppm.

(In NMR spectral data we referred to numbers of the atoms corresponding to the numbering as shown by formula III.)

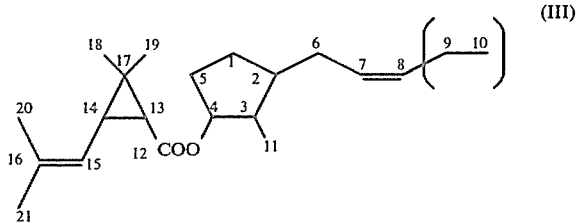

EXAMPLE 4

The process according to Example 3 is carried out except that 150 mg. (0.47 millimoles) of 1β-hydroxy-2β-(but-2-cis-enyl)-3-methylene-cyclopentan-4β-yl-(+)-transchrysanthemate are used as starting material. Thus 137 mg. of 3-methyl-2-(but-2-cis-enyl)-1-oxo-cyclopent-2-en-4β-yl-(+)-trans-chrysanthemate are obtained. Yield: 91.3%.

The physical constants of the above product are identical with those of the compound prepared according to Example 1.

EXAMPLE 5

The process according to Example 2 is carried out except that 1.3 g. (4.2 millimoles) of 1β-hydroxy-2β-(prop2-enyl)-3-methylene-cyclopentane-4β-yl-(+)-trans-chrysanthemate are used as starting material.

Thus 1.14 g. of 3-methyl-2-(prop-2-enyl)-1-oxo-cyclopent-2-en-4β-yl-(+)-transchrysanthemate are obtained. Yield: 88%. (S-bioallethrin).

$R_f$=0.68 (60 $F_{254}$ "Merck" silica gel plate; developing agent 4:1 mixture of petrolether and ethyl acetate); $[α]_D^{20}$= −22° (c=0.7, hexane).

NMR (CDCl$_3$) δ: 4.96 (m, 1H, H-4), 1.41 (m, 1H, H-13), 1.7 (m, 1H, H-14), 5.08–5.6 (m, 3H, H-7 and H-8, H-8), 5.7 (m, 1H, H-15), 2.05 (s, 3H, H-11), 1.14 and 1.27 ((s and s, 3H and 3H, H-18 and H-19), 1.73 (s, 6H, H-20 and H-21) ppm.

What we claim is:

1. A process for the preparation of an optically active or racemic compound of the formula I

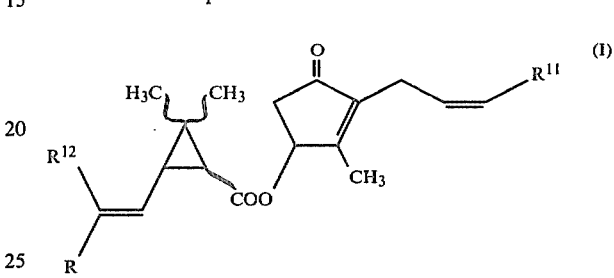

wherein

R$^{11}$ is straight or branched chain lower alkyl or 1-alkenyl or hydrogen;

R and R$^{12}$ are the same or different and are hydrogen, halogen or lower alkyl or one of the moieties R and R$^{12}$ is lower alkoxy-carbonyl;

the ⁓ valency bonds represent α- and/or β-configuration; and the—bonds represent β-configuration, which comprises treating an optically active or racemic compound of the formula II

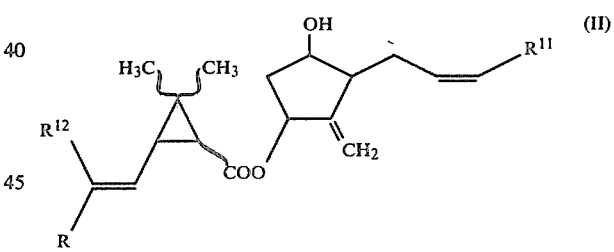

with an oxidizing agent in an aprotic inert organic solvent wherein the oxidizing agent is capable of oxidizing the secondary hydroxy group of the compound of the formula II without damaging other parts of the compound.

2. The process defined in claim 1 wherein the oxidizing agent used oxidizes with the formation of a sulfoxonium type intermediate product.

3. The process defined in claim 1 wherein the oxidizing agent contains a chromium$^{6+}$ atom.

4. The process defined in claim 1 wherein the oxidation is carried out with a pyridinium-chlorine-chromate reactant in methylene chloride as reaction medium.

5. The process defined in claim 1 wherein tthe oxidation is carried out by using a mixture of chromium(-VI)oxide, sulfuric acid and water in acetone as inert solvent.

6. The process defined in claim 1 wherein the oxidation is carried out by using a N-chloro-succinimide/- dimethyl sulfide reactant in toluene as the reaction medium.

7. The process defined in claim 1 for the preparation of 3-methyl-2-(but-2-cis-enyl)-1-oxo-cyclopent-2-en-4β-yl-(+)-trans-chrysanthemate which comprises oxidizing 1β-hydroxy-2β-(but-2-cis-enyl)-3-methylene-cyclopentane-4β-yl-(+)-trans-chrysanthemate in said aprotic inert organic solvent.

8. The process defined in claim 1 for the preparation of 3-methyl-2-(pent-2-cis-enyl)-1-oxo-cyclopent-2-en-4β-yl-(+)-trans-chrysanthemate which comprises oxidizing 1β-hydroxy-2β-(pent-2-cis-enyl)-3-methylene-cyclopentane-4β-yl-(+)-trans-chrysanthemate in said aprotic inert organic solvent.

9. The process defined in claim 1 for preparation of 3-methyl-2-(prop-2-enyl)-1-oxo-cyclopent-2-en-4β-yl-(+)-trans-chrysanthemate which comprises oxidizing 1β-hydroxy-2β-(prop-2-enyl)-3-methyl-cyclopentane-4β-yl-(+)-trans-chrysanthemate in said aprotic inert organic solvent.

10. The process defined in claim 1 wherein the starting material is a compound of the formula II wherein $R^{11}$ is hydrogen or lower alkyl, and R and $R^{12}$ and are lower alkyl.

* * * * *